United States Patent
Derrieu et al.

(10) Patent No.: US 6,599,888 B1
(45) Date of Patent: Jul. 29, 2003

(54) CHONDROITIN SULPHATE AND CHITOSAN COMPOSITIONS FOR TREATING RHEUMATIC DISORDERS

(75) Inventors: Guy Derrieu, Cagnes-sur-Mer (FR); Jean-Luc Pougnas, Saint Laurent du Var (FR)

(73) Assignee: Virbac, Carros (FR)

( * ) Notice: Subject to any disclaimer, the term of this patent is extended or adjusted under 35 U.S.C. 154(b) by 0 days.

(21) Appl. No.: 09/743,259

(22) PCT Filed: Mar. 22, 2000

(86) PCT No.: PCT/FR00/00721

§ 371 (c)(1),
(2), (4) Date: Feb. 22, 2002

(87) PCT Pub. No.: WO00/56275

PCT Pub. Date: Sep. 28, 2000

(30) Foreign Application Priority Data

Mar. 22, 1999 (FR) .............................................. 99 03538

(51) Int. Cl.$^7$ ........................ A61K 31/72; A61K 41/36; C07H 5/06
(52) U.S. Cl. ........................ 514/54; 536/123.1; 424/439
(58) Field of Search ...................................... 514/55, 54

(56) References Cited

U.S. PATENT DOCUMENTS

| | | | |
|---|---|---|---|
| 5,145,841 A | | 9/1992 | Cullis-Hill et al. |
| 5,166,187 A | | 11/1992 | Collombel et al. |
| 5,364,845 A | | 11/1994 | Henderson |
| 5,587,363 A | * | 12/1996 | Henderson .................. 514/54 |
| 5,622,834 A | * | 4/1997 | Vournakis et al. ............ 435/84 |

FOREIGN PATENT DOCUMENTS

| | | | |
|---|---|---|---|
| EP | 0 454 599 | 10/1991 | |
| EP | 0 637 450 | 2/1995 | |
| EP | 0 941 735 | 9/1999 | |
| GB | 2 266 239 | 10/1993 | |
| GB | 2 286 528 | 8/1995 | |
| WO | 94 00135 | 1/1994 | |
| WO | 96 02259 | 2/1996 | |
| WO | 98 22114 | 5/1998 | |
| WO | WO 98/22114 | * 6/1998 | .......... A61K/31/70 |
| WO | 98 58011 | 12/1998 | |

OTHER PUBLICATIONS

Database WPO, Week 199441; Derwent Publications Ltd., London, GB; AN 1994–329956; XP002144836.
06 256221; Japan (Kibun Food Chemiphar KK) (Sep. 13, 1994); abstract.

* cited by examiner

Primary Examiner—James O. Wilson
Assistant Examiner—Ganapathy Krishnan
(74) Attorney, Agent, or Firm—Lowe Hauptman Gilman & Berner, LLP

(57) ABSTRACT

The subject of the present invention is the use of a preparation comprising:

a) from 1 to 50% by weight, relative to the total weight of the preparation, of at least one compound chosen from chondroitin sulfates and their salts, and b) from 1 to 66% by weight, relative to the total weight of the preparation, of at least one compound chosen from chitosan, its salts, its derivatives and the salts of these derivatives, for the preparation of a composition for the prevention or treatment of rheumatic conditions by the general route, and, in particular, for the prevention or treatment of degenerative arthropathies.

22 Claims, No Drawings

CHONDROITIN SULPHATE AND CHITOSAN COMPOSITIONS FOR TREATING RHEUMATIC DISORDERS

The subject of the present invention is the use of preparations based on chondroitin sulfate and chitosan for the preparation of compositions intended for the prevention or treatment of rheumatic conditions and, in particular, degenerative arthropathies, by the general route.

The joints and the various connective tissues of which they consist (cartilages, fibrocartilages, synovial membranes, ligaments and the like) are constantly subjected to mechanical stresses and to stresses which may lead to inflammatory pathologies such as arthritis or degenerative pathologies such as osteoarthritis, which are responsible for their blockage. These conditions may be acute at the level of the joints in the neck, the shoulders, the back, the hips, the forelimbs such as the elbows and the wrists, the hindlimbs such as the knees and the ankles, as well as the fingers or the toes. These pathologies are very frequent and affect both humans and animals.

Mainly two families of antiinflammatory compounds are used in human and veterinary rheumatology: the glucocorticosteroids and the NSAIDs (or nonsteroidal antiinflammatory drugs: salycilates, indoles and related compounds, propionics, pyrazoles, anthranylines and the like). Although relieving pain and reducing the inflammatory state of connective tissues during their use, these compounds have only a pain-relieving function and do not allow a return to the normal state by the reconstitution of the tissues. Thus, these treatments are in the long term ineffective, or even harmful, because they block the natural processes for the defence of the body and lead to a destruction of the connective tissues.

When they are subjected to exercise, stress and in particular when they are the seat of lesions, the connective tissues naturally produce large quantities of collagen and of proteoglycans (PG), which are major components of these tissues, so as to become reconstituted.

These compounds, as well as their mechanisms of biosynthesis and of action, are perfectly known and described in the literature.

Collagen is manufactured from amino acids, in particular from proline, glycine and lysine, and its biosynthesis is stimulated by the presence of glucosamine.

Proteoglycans, which are large macromolecular complexes, for their part, consist of modified long chains of sugars called glycosaminoglycans (GAG) such as hyaluronic acid, chondroitin sulfates or alternatively heparin, and of which glucosamine is a precursor.

In the processes for the reconstitution of connective tissues, collagen and proteoglycans form a matrix which confers on the tissues their mechanical properties. However, the processes for the in vivo biosynthesis of collagen and of proteoglycans from precursor molecules are relatively long, which constitutes an impediment to the repair of these tissues.

Accordingly, to promote the reconstitution of the connective tissues, some treatments consist in bringing exogenous precursor molecules into the body.

Thus, it has been proposed, in U.S. Pat. No. 5,145,841, to treat rheumatic conditions of an inflammatory nature and, in particular, arthritis, by injecting, either directly into the tissues where the inflammation exists, or into the general circulation (by the intramuscular, subcutaneous or intravenous route), compositions comprising at least two compounds chosen from hyaluronic acid, corticoids and sulfated polysaccharides of the heparin sulfate and chondroitin sulfate type, the latter being preferably used in the form of complexes with a metal ion.

Moreover, U.S. Pat. No. 5,364,845 and No. 5,587,363 as well as European patent application No. 0 693 928 describe compositions intended for the protection and repair of the connective tissue, which are, for their part, intended to be administered by the oral route and which consist of combinations between an amino sugar and a glycosaminoglycan with optionally a manganese salt. The amino sugar is chosen from glucosamine, its salts and mixtures thereof, while the glycosaminoglycan is chosen from chondroitin sulfates, their salts and mixtures thereof.

Although these combinations have shown a synergistic effect compared with compositions containing either glucosamine alone, or chondroitin sulfate alone, it is known that the exogenous molecules thus provided to the body and, in particular, the chondroitin sulfates and their salts, are substantially degraded in vivo. This degradation reduces the quantity of precursor molecules capable of being used for the reconstruction of the connective tissue and, consequently, the expected therapeutic benefit, in particular in the case where these molecules are administered by the oral route.

It is therefore desirable to have compositions with enhanced therapeutic efficacy.

Chitosan is a polysaccharide which is obtained by a more or less total N-deacetylation of the chitin. The hydrolysis of chitin, the homopolymer of N-acetyl-D-glucosamine, and of chitosan leads to the formation of glucosamine, the principal precursor of the sugars involved in the synthesis of glycosaminoglycans.

Chitosan has recognized film-forming, reconstituting, antibacterial, antifungal and wound-healing properties which have led to its use in medicine, in particular as a constituent of biomaterials intended to be used in orthopedic, plastic and reconstructive surgery, either as artificial skin, or as matrix capable of allowing bone, nerve or skin cells to become regenerated. These uses are for example described in U.S. Pat. No. 5,166,187 and in international application No. WO 96/02259.

Recently, DENUZIERE et al. (*Electrophoresis*, 1997, 18, 745–750) have shown, in vitro, that chitosan protected, at a physiological pH, chondroitin sulfates from hydrolysis when these sulfates were complexed beforehand, in aqueous medium, with chitosan.

Chitosan, its salts and its derivatives are defined in greater detail in many books, in particular in the book by MUZZARELLI entitled "The Polysaccharides" (1985) Academic-Press.

However, the Inventors have observed that the combination of a chondroitin sulfate or of a salt thereof with either chitosan or a salt or a derivative thereof, or alternatively a salt of such a derivative, makes it possible, unexpectedly, to obtain compositions which exhibit a therapeutic effect/dose of chondroitin sulfate ratio markedly greater than that exhibited by the compositions provided in U.S. Pat. No. 5,364,845, U.S. Pat. No. 5,587,363 and EP-A-0 693 928.

Thus, for chondroitin sulfate doses administered which are equivalent, or even lower, compositions comprising both chondroitin sulfate (or a salt of such a sulfate) and chitosan (or a salt, a derivative or a salt of a derivative of chitosan) have been found to improve more rapidly the clinical signs than the composition provided in the abovementioned state of the art; in particular, the compositions prepared by the Inventors have shown that they made it possible to reduce more rapidly the symptoms of pain and to improve mobility more quickly, as well as the tolerance to exercise.

The present invention therefore relates to the use of a preparation comprising:

a) from 1 to 50% by weight, relative to the total weight of the preparation, of at least one compound chosen from chondroitin sulfates and their salts, and b) from 1 to 66% by weight, relative to the total weight of the preparation, of at least one compound chosen from chitosan, its salts, its derivatives and the salts of these derivatives, for the preparation of a composition for the prevention or treatment of rheumatic conditions by the general route.

For the purposes of the present invention, the expression "general route" is understood to mean any route for administration of the composition allowing systemic distribution of the active ingredients which it contains, that is to say the enteral (oral and rectal) route, the parenteral (intramuscular, intravenous and subcutaneous) route and the transdermal route, excluding any in situ application of said composition.

According to a first preferred feature of the invention, the preparation comprises a sodium chondroitin sulfate.

According to another preferred feature of the invention, the preparation comprises a compound chosen from chitosan, its salts of adipic acid, ascorbic acid, formic acid, glycolic acid and lactic acid, N-acylchitosans, N-carboxyalkylchitosans, N-carboxy-acylchitosans, O-carboxyalkylchitosans, deoxyglycit-1-ylchitosans, hydroxyalkylchitosans and their salts obtained by addition with organic or inorganic acids.

Preferably, the chitosan is obtained by N-deacetylation of at least 80% of the chitin and is chosen from those provided by the Japanese companies KOYO, reference SK-400F80 or SK-50SEP with a deacetylation greater than 85%, KATAKURA, reference CTA-1 or CTA-2 with a deacetylation greater than 90% for the first and greater than 80% for the second, YAIZU, reference LL or LL-40 with a deacetylation greater than 80%, KYOWA, reference HW with a deacetylation greater than 85%.

Advantageously, the preparation comprises, furthermore, an effective quantity of one or more inhibitor of free radicals which participate in the processes for the protection, treatment and reconstitution of the connective tissues.

There may be mentioned, by way of examples of anti-free radicals capable of being used in the compositions, vitamin E and its derivatives, vitamin C and its derivatives (in particular manganese ascorbate and/or glucosamine ascorbate), bioflavanoids, superoxide dismutase and its salts, and extracts of plants known to exhibit anti-free radical effects, such as rosemary essential oil.

Advantageously, the preparation also comprises any component facilitating or participating in the biosyntheses or in the processes for the protection, treatment and reconstitution of the connective tissues, such as trace elements in organic or inorganic forms (manganese, copper, iron, zinc and the like), vitamins and nutrients.

In accordance with the invention, the preparation is capable of being used to prepare a pharmaceutical composition, in which case the latter is preferably formulated to be administered by the oral route.

As a variant, the preparation may also be used to prepare a dietary supplement capable, upon daily administration or as a cure in the form of a dietary supplement, of preventing or of treating rheumatic conditions.

The pharmaceutical composition or the dietary supplement thus prepared are capable of being provided in various forms suitable for oral administration: solid (tablets, gelatin capsules, lozenges to be chewed, granules, powders for oral suspension, and the like), pasty or liquid (syrups, oral solutions or suspensions, and the like). Accordingly, the preparation is capable of comprising, in addition, various additives (binding agents, diluents, lubricants, flow-enhancing agents, colorings, taste-enhancing agents, solvents and the like) which are chosen according to the form which it is desired to give the pharmaceutical composition or the dietary supplement.

The composition prepared according to the invention, whether it be pharmaceutical, or whether it be a dietary supplement, preferably comprises quantities of chondroitin sulfate and of chitosan which make it possible to provide, per kg of live weight and per day:

a) from 5 to 25 mg of sodium chondroitin sulfate, and b) from 5 to 50 mg of chitosan, and this being in one or more doses.

In a particularly preferred manner, this composition comprises quantities of chondroitin sulfate and of a chitosan having a degree of N-deacetylation at least equal to 80%, making it possible to provide, per kg of live weight and per day:

a) from 10 to 20 mg and, preferably, about 15 mg of sodium chondroitin sulfate, and b) from 10 to 20 mg and, preferably, about 15 mg of chitosan, in one or more doses.

It is capable of being used both in animals and in humans in the prevention and treatment of any rheumatic pathologies, whether they are of inflammatory, metabolic or degenerative origin, chronic or acute.

By way of examples of such pathologies, there may be mentioned arthritis, rheumatoid arthritis, ankylosing spondylarthritis (or related syndromes such as Fiessinger-Leroy-Reiter syndrome, arthropatic psoriasis), scapulo-humeral periarthritis, tendinitis, bursitis, osteoarthritis (cervical osteoarthritis, vertebral osteoarthritis, coxarthrosis, and the like) and gout.

The following example is intended to illustrate the invention without however limiting its scope.

EXAMPLE

1. Procedure 3 groups of 20 dogs with no restriction of breed, age, sex, chosen in a weight range going from 5 to 35 kg and having osteoarthritis with chronic manifestation resulting in lameness of a limb for at least 1 month, were treated and followed by their owners and by vets.

The presence of at least one of the osteoarthritic lesions, appearing on the clinical card, in one or more joints of the relevant limb (including the joint in the shoulder and the hip) is confirmed from an X-ray dating from less than three months or taken on the day when the animals were selected.

All the antiinflammatory treatments by the oral or injectable route and all the chondroprotective products covered were stopped at least 7 days before selecting the animals.

Dog tablets of formulations A and C are prepared according to techniques known to persons skilled in the art and commercial capsules of formulation B are used.

The tablets of formulation A correspond to a composition according to the invention combined with suitable excipients.

The capsules of formulation B correspond to the commercial American products made according to the method described in patents U.S. Pat. Nos. 5,364,845 and No. 5,587,363. B1 corresponds to the capsules called "Cosequin (Regular Strength)" and B2 corresponds to the capsules "Cosequin (Double Strength)".

The tablets of formulation C correspond to a composition which comprises quantities of chondroitin sulfate and of glucosamine which are identical to those present in formulation B1, but which is provided in the form of tablets which were prepared like tablets A.

The final content of tablets A and C and of capsules B1 and B2 is illustrated in Table 1 below. The quantities are expressed as percentages by weight of the total weight of the composition.

TABLE 1

| FORMULATIONS | A | B1 | B2 | C |
|---|---|---|---|---|
| Sodium chondroitin sulfate | 22.73 | | | 18.185 |
| Chitosan | 22.73 | | | |
| Appetite-enhancing agent | 10.0 | | | |
| Excipient for tablets | 44.54 | | | 55.54 |
| Glucosamine HCl 99+% | | 51.23 | 51.23 | 22.73 |
| Sodium chondroitin sulfate 95% + mixture of glucosaminoglycans 5% | | 40.985 | 40.985 | |
| Manganese ascorbate | | 7.785 | 7.785 | 3.455 |
| that is as ascorbate | | 6.76 | 6.76 | 3 |
| that is as manganese | | 1.025 | 1.025 | 0.455 |
| Weight of one tablet | 660 mg | | | 1100 mg |
| Weight in one capsule | | 488 mg | 976 mg | | a) mode of treating the first group

Each animal in the first group is treated with composition A in accordance with the invention and provided in the form of tablets, in an amount of 1 dose per day, the number of tablets being from 1 to 3 tablets and ½ per dose according to the weight of the animal, for 6 weeks.

Each animal receives about 15 mg of sodium chondroitin sulfate (ACS) and 15 mg of chitosan (KATAKURA, reference CTA - 1) per kg of live weight and per day.

b) mode of treatment of the second group

Each animal in the second group is treated with composition B1 [Cosequin (Regular Strength)] or B2 [Cosequin (Double Strength)] in an amount of:

2 capsules per day of B1 for 6 weeks for dogs having a body weight of between 4.5 and 11.35 kg, 2 capsules of B2 for 6 weeks for dogs having a body weight of between 11.35 and 22.24 kg, 3 capsules of B2 for 6 weeks for dogs having a body weight of between 22.7 and 45.4 kg.

Each animal thus receives about 30 mg of chondroitin sulfate and 37.5 mg of glucosamine per kg of live weight and per day.

c) mode of treating the third group

Each animal in the second group is treated with composition C in an amount of:

2 tablets for dogs having a body weight of between 4.5 and 11.35 kg, 4 tablets for dogs having a body weight of between 11.35 and 22.24 kg, 6 tablets for dogs having a body weight of between 22.7 and 45.4 kg.

Each animal thus receives about 30 mg of chondroitin sulfate and 37.5 mg of glucosamine per kg of live weight and per day.

d) parameters studied:

The owner of each animal studies, with reference to the behavior of their animal before treatment:

the ease with which the animal moves and lameness in the animal during its movements, the suffering of the animal and spontaneous complaints or complaints when it is stroked.

The vet, during the visits at 30 and 60 days after the beginning of the treatment, studies:

the difficulty of getting up and going over an obstacle, tolerance to exercise, assessed by questioning the owner, lameness, assessed by clinical examination, pain, assessed by palpation-pressure and by mobilization of the joint, and amplitude between the maximum bending and extension of the joint compared with a healthy joint, taking into account the dog's breed.

The first two parameters assessed by the vet take into account the owner's opinion.

The five parameters are assessed by the vet according to the following scale:

cure, if all the parameters have become normal, substantial improvement, if at least 3 parameters have become normal, partial improvement, if 1 or 2 parameters have become normal, failure, if none of the 5 parameters has become normal.

2. Results a) 30 days after the beginning of the treatment:

On visiting the vet, 30 days after the beginning of the treatment, the results expressed in Table 2 below are observed:

TABLE 2

| | Failure | Partial improvement | Substantial improvement | Cure |
|---|---|---|---|---|
| Formulation A | 35% | 50% | 15% | — |
| Formulation B | 55% | 40% | 5% | — |
| Formulation C | 55% | 45% | — | — |

The owners of the dogs in group A reported to the vet in 13 cases out of 20 that, from the tenth day of treatment, a general improvement in the state of health of their animal appeared, indicating a spontaneous mobility of the animal and a disappearance of the pain, often felt during strokes.

After treatment with composition A according to the invention, a significant reduction in the failure rate and a significant increase in the number of animals showing a substantial improvement is observed.

b) 60 days after the beginning of the treatment:

On visiting the vet, 60 days after the beginning of the treatment, the results expressed in Table 3 below are observed:

TABLE 3

| | Failure | Partial improvement | Substantial improvement | Cure |
|---|---|---|---|---|
| Formulation A | 15% | 20% | 65% | — |
| Formulation B | 35% | 25% | 40% | — |
| Formulation C | 40% | 25% | 35% | — |

Formulation A according to the invention appears clearly as the one which exhibits the best therapeutic effect, whereas the treated animals received with this formulation a quantity of chondroitin sulfate which was half that which was administered to them with formulations B and C.

A significant reduction in the failure rate and a significant increase in the number of animals showing a substantial improvement is observed after treatment with composition a according to the invention.

What is claimed is:

1. A method for the treatment of rheumatic conditions in an animal comprising the steps of:
   A. admixing:
      a) at least one compound selected from the group consisting of chondroitiii sulfates and their pharmaceutically acceptable salts, and
      b) at least one compound selected from the group consisting of chitosan, its pharmaceutically acceptable salts, its derivatives and pharmaceutically acceptable salts of its derivatives;
   to produce an admixture comprising about 1–50 weight %, based on the weight of said admixture, of said compound a), and about 1–66 weight %, based on the weight of said admixture, of said compound b); and
   B. administering to an animal in need thereof, by a general administration route, a quantity of said admixture sufficient to treat a rheumatic condition that has already developed in said animal.

2. The method as claimed in claim 1 wherein said animal is human.

3. The method as claimed in claim 1 wherein said compound a) comprises a sodium chondroitin sulfate.

4. The method as claimed in claim 1 wherein said compound b) comprises a compound selected from the group consisting of chitosan, a chitosan salt of adipic acid, a chitosan salt of ascorbic acid, a chitosan salt of formic acid, glycolic acid, a chitosan salt of lactic acid, N-acylchitosans, N-carboxyalkylchitosans, N-carboxy-acylchitosans, O-carboxyalkylchitosans, deoxyglycit-1-ylchitosans, hydroxyalkylchitosans and their salts.

5. The method as claimed in claim 1, in which the chitosan is at least 80% deacrtylated.

6. The method as claimed in claim 1 wherein said admixture further comprises effective quantity of at least one inhibitor of free radicals.

7. The method as claimed in claim 1 further comprising assembling said admixture for oral administration, and orally administering said admixture.

8. The method as claimed in claim 1 further comprising formulating said admixture as a dietary supplement and administered said admixture as a dietary supplement.

9. The method as claimed in claim 1 further comprising admixing a sufficient quantity of said sodium chondroitin sulfate to provide about 5 to 25 mg thereof per kg of live body weight of said animal per day and a sufficient quantity of said chitosan to provide about 5 to 50 mg thereof per kg of live animal weight per day.

10. The method as claimed in claim 1 further comprising admixing a) and b) compounds having a degree of deacetylation of at least about 80%; and admixing a sufficient quantity of said deacetylated a) compound to provide about 10 to 20 mg of said a) compound per kg of live body weight of said animal per day with a sufficient quantity of said deacetylated b) compound to provide about 10 to 20 mg of said b) compound per kg of live body weight of said animal per day.

11. The method as claimed in claim 1 further comprising admixing a) and b) compounds having a degree of deacetylation of at least about 80%; and admixing a sufficient quantity of said deacetylated a) compound to provide about 15 mg of said a) compound per kg of live body weight of said animal per day with a sufficient quantity of said deacetylated b) compound to provide about 15 mg of said b) compound per kg of live body weight of said animal per day.

12. The method as claimed in claim 1 further comprising administering a quantity of said admixture after the onset of osteoarthritis in said animal and in sufficient quantity to treat said osteoarthritis in said animal.

13. A composition comprising about 1–50% by weight of at least one first compound selected from the group consisting of chondroitin sulfates and their pharmaceutically acceptable salts, and about 1 to 66 % by weight of at least one second compound selected from the group consisting of chitosan, its pharmaceutically acceptable salts, its derivatives and pharmaceutically acceptable salts of its derivatives;
   wherein said composition has the property of treating rheumatic conditions to ameliorate the effects thereof.

14. The composition as claimed in claim 13 formulated as a dietary supplement.

15. The composition as claimed in claim 13 formulated as a pharmaceutical for treatment of rheumatic conditions.

16. The composition as claimed in claim 13 comprising sodium chondroitin sulfate.

17. The composition as claimed in claim 13 wherein said second compound is at least one selected from the group consisting of chitosan, a chitosan salt of adipic acid, a chitosan salt of ascorbic acid, a chitosan salt of formic acid, glycolic acid, a chitosan salt of lactic acid, N-acylchitosans, N-carboxyalkylchitosans, N-carboxy-acyl-chitosans, O-carboxyalkylchitosans, deoxyglycit-1-ylchitosans, hydroxyalkylchitosans and their salts.

18. The composition as claimed in claim 13 wherein said chitosan is at least about 80% deacetylated.

19. The composition as claimed in claim 13 further comprising at least one additional compound that is an inhibitor of free radicals.

20. The composition as claimed in claim 13 comprising said first compound in a quantity sufficient to provide about 5 to 25 mg per kg of live animal weight per day and comprising said second compound in a quantity sufficient to provide about 5 to 50 mg of live animal weight per day.

21. The composition as claimed in claim 13 comprising a sufficient amount of said first compound, that has been at least about 80% deacetylated, to provide about 10 to 20 mg per kg of live animal weight per day and a sufficient amount of said second compound, that has been at least about 80% deacetylated, to provide about 10 to 20 mg per kg of live animal weight per day.

22. The composition as claimed in claim 13 comprising a sufficient amount of said first compound, that has been at least about 80% deacetylated, to provide about 15 mg per kg of live animal weight per day and a sufficient amount of said second compound, that has been at least about 80% deacetylated, to provide about 15 mg per kg of live animal weight per day.

* * * * *